United States Patent [19]
Bauer et al.

[11] 3,957,828
[45] May 18, 1976

[54] 3-AMINOALKYL-1,3-DIHYDRO-3-PHENYLSPIRO[ISOBENZOFURANS]

[75] Inventors: Victor J. Bauer, Somerville; Helen H. Ong, Whippany, both of N.J.

[73] Assignee: American Hoechst Corporation, Bridgewater, N.J.

[22] Filed: Aug. 29, 1974

[21] Appl. No.: 501,669

[52] U.S. Cl. .............................. 424/283; 260/293.58; 260/293.67; 260/293.83; 260/307 F; 260/327 TH; 424/267; 424/275; 260/345.9
[51] Int. Cl.$^2$ ................. C07D 493/10; A61K 31/35
[58] Field of Search .................... 260/345.9, 345.1

[56] References Cited
OTHER PUBLICATIONS

Migrdichian, "Organic Synthesis," Reinhold Publishing Corp., New York (1957), pp. 736–738.

Primary Examiner—G. Thomas Todd
Attorney, Agent, or Firm—Curtis, Morris & Safford

[57] ABSTRACT

Substituted 3-aminoalkyl-1,3-dihydro-3-phenylspiro[isobenzofurans] possessing tranquilizing properties, and process for the preparation thereof are described.

6 Claims, No Drawings

3-AMINOALKYL-1,3-DIHYDRO-3-PHENYL-SPIRO[ISOBENZOFURANS]

This invention relates to 3-aminoalkyl-1,3-dihydro-3-phenylspiro[isobenzofurans] possessing tranquilizing properties, the physiologically tolerable acid addition salts thereof, and process for the preparation thereof.

To the best of our knowledge, the compounds of the present invention have not heretofore been described.

The compounds of the invention conform to the general formula:

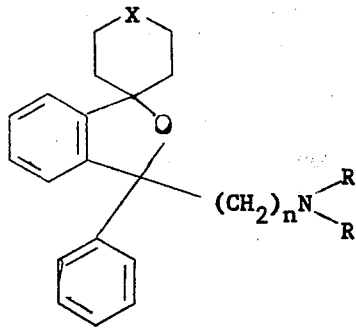

wherein R is alkyl of from 1 to 4 carbon atoms, X represents O, S or $$\underset{CH_3}{\overset{|}{N,}}$$

and n is the integer 2 or 3. Preferred compounds are those in which R is methyl.

The compounds of the present invention can be prepared by one of two multi-step sequences of reactions as described below.

METHOD A 1. 2-Bromobenzhydrol is converted to 2-bromobenzhydryl methyl ether, preferably in an acid medium and with methanol as both a solvent and as a methylating agent.

2. The bromine atom of the 2-bromobenzhydryl methyl ether is then replaced by lithium by reacting with an alkyllithium of from 1 to 4 carbon atoms such as n-butyllithium. This bromine replacement is effected in the presence of an inert organic solvent, at low temperature, for from a few minutes to 6 hours. A preferred solvent is a mixture of tetrahydrofuran and hexane. The reaction temperature is preferably from −30° to −70°C. The resulting compound is reacted, in situ, with a compound of the formula:

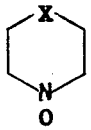

in which X is as defined earlier, at a low temperature for from a few minutes to 18 hours to produce a compound of the formula:

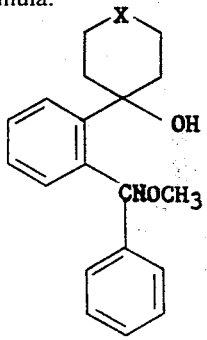

A preferred reaction temperature is from −30° to −70°C.

3. This alcohol is treated with an acid to produce a 1,3-dihydro-3-phenylspiro[isobenzofuran] of the formula:

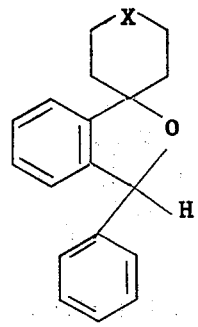

One preferred method is by reacting the alcohol in a refluxing mixture of glacial acetic acid and concentrated hydrochloric acid.

4. The above 1,3-dihydro3-phenylspiro[isobenzofuran] is treated with an alkyllithium of from 1-4 carbon atoms, such as n-butyllithium, in the presence of an organic solvent, such as tetrahydrofuran, for from a few minutes to 5 hours. Then a sample of a dialkylaminoethyl halide or dialkylaminopropyl halide in an inert organic solvent is added and allowed to react for from a few minutes to 24 hours to produce a compound of the invention. Preferred halides are chlorides.

METHOD B 1. 2-Bromo-N-(1-hydroxy-2-methyl-2-propyl) benzamide is cyclized to 2-(2-bromophenyl-4,4-dimethyl-2-oxazoline by treatment with a dehydrating agent such as thionyl chloride, phosgene or phosphorus oxychloride at a temperature of −20° to −40°C. in the presence or absence of a solvent such as toluene, pyridine, or chloroform for from 30 minutes to 24 hours.

2. The oxazoline is converted to the Grignard reagent under the usual conditions, such as by a reaction with magnesium at a temperature of preferably 25° to 65°C. in a solvent such as diethyl ether or tetrahydrofuran for a time of preferably 15 minutes to 24 hours with or without the assistance of an initiator such as iodine or 1,2-dibromoethane. The reaction of the above Grignard reagent with a compound of the formula:

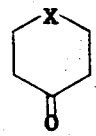

wherein X is as defined earlier, at a temperature of from −60° to 100°C., for from 15 minutes to 24 hours, provides an adduct of the formula:

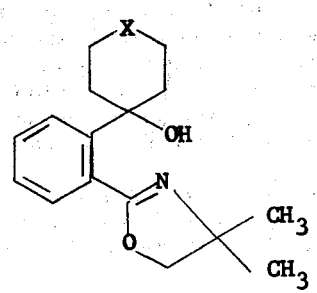

3. This adduct is treated with an acid, such as aqueous hydrochloric or sulfuric, at a temperature of from 25° to 125°C., for a time of from 10 minutes to 24 hours, with or without a solvent such as water, ethanol, or acetic acid to provide a 1,3-dihydrospiro[isobenzofuran]-3-one of the formula:

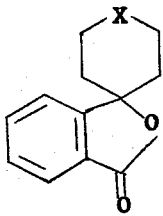

4. The 1,3-dihydrospiro[isobenzofuran]-3-one is reacted with phenyllithium at a temperature of from −60° to 100°C., in the presence of a solvent such as hexane, toluene, ether or tetrahydrofuran for a time of from 10 minutes to 24 hours, to provide a 1,3-dihydro-3-hydroxy-3-phenylspiro[isobenzofuran] of the formula:

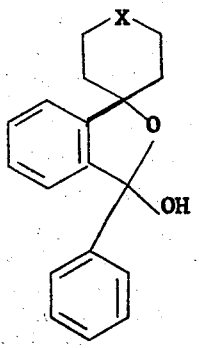

5. The 1,3-dihydro-3-hydroxy-3-phenylspiro[isobenzofuran] is reacted with a reducing agent such as lithium aluminum hydride, by a method known to the art to the corresponding diol of the formula:

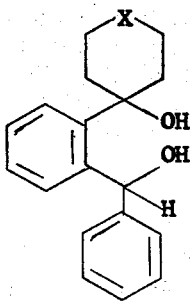

6. The diol is cyclized by treatment with an acid, such as hydrochloric, formic, or p-toluenesulfonic, with or without a solvent, such as toluene or acetic acid, at a temperature of from 25° to 150°C., for from 5 minutes to 24 hours, to provide a 1,3-dihydro-3-phenylspiro[isobenzofuran] as described in Step 3 of Method A.

7. The above 1,3-dihydro-3-phenylspiro[isobenzofuran] is converted to a compound of the invention according to the procedure of Step 4 of Method A.

The compounds of the invention are useful as tranquilizers due to their depressant action on the central nervous system of mammals. This activity is demonstrated by the following procedure. Groups of four mice are given intraperitoneally various dose levels of a compound and observed continuously for at least 4 hours for overt behavioral, reflex, or autonomic effects. Results are expressed in terms of the minimum effective dose (MED) causing a definitive effect. The following compounds, 1,3-dihydro-3-dimethylaminoethyl-1'-methyl-3-phenylsprio[isobenzofuran-1,4'-piperidine] dihydrochloride, 1,3-dihydro-3-(3-dimethylaminopropyl)-1'-methyl-3-phenylspiro[isobenzofuran-1,4'-piperidine] dihydrochloride, 3-dimethylaminoethyl-1,2',3,3',5',6'-hexahydro-3-phenylspiro-[isobenzofuran-1,4'-thiopyran] hydrochloride, 3-(3-dimethylaminopropyl)-1,2',3,3',5',6'-hexahydro-3-phenylspiro[isobenzofuran-1,4'-thiopyran], 3-dimethylaminoethyl-1,2',3,3',5',6'-hexahydro-3-phenylspiro[isobenzofuran-1,4'-pyran] hydrochloride, and 3-(3-dimethylaminopropyl)-1,2',3,3',5',6'-hexahydro-3-phenylspiro[isobenzofuran-1,4'-pyran] hydrochloride exhibit MEDs of 30,30,30,30, 10, and 30 mg./kg. of body weight respectively. These data demonstrate that the compounds are useful for depressing the central nervous systems of mammals with doses ranging from 0.5 to about 50 mg./kg. of body weight per day.

The compounds of the present invention may be administered to a patient by any convenient route such as orally, intramuscularly, intravenously, subcutaneously, or intraperitoneally. The preferred route of administration is oral, for example, with an inert diluent or with an edible carrier or in gelatin capsules or tablets.

For the purpose of oral therapeutic administration, the active compounds of this invention may be incorporated with excipients and used in the form of tablets, troches, capsules, elixirs, suspensions, syrups, wafers, chewing gum, and the like. These preparations should contain at least 0.5% of active compound, but may be varied depending upon the particular form and may conveniently be between 7% to about 70% by weight of the unit. The amount of active compound in such compositions is such that a suitable dosage will be obtained. Preferred compositions and preparations according to the present invention are prepared so that an oral dosage unit form contains between 10 and 200 milligrams of active compound.

The tablets, pills, capsules, troches, and the like may also contain the following ingredients: a binder such as gum tragacanth or gelatin; an excipient such as starch or lactose, a disintegrating agent such as alginic acid, potato starch and the like; a lubricant such as magnesium stearate; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or both. A syrup may contain, in addition to the active compounds sucrose as a sweetening agent, and certain preservatives, dyes and colorings, and flavors. Materials used in preparing these various compositions must be pharmaceutically pure and non-toxic in the amounts utilized.

Acids useful for preparing the acid addition salt (pharmaceutically acceptable) include inorganic acids such as hydrochloric, hydrobromic, sulfuric, nitric, phosphoric, and perchloric acids, as well as organic acids such as fumaric tartaric, citric, acetic, maleic, and ethane disulfonic acids.

EXAMPLE I a. A solution of 730 g. of 2-bromobenzhydrol and 25 l. of methanol is slowly heated to reflux over a 2 hour span while a stream of hydrogen chloride gas is bubbled into the solution. The solution is refluxed for 24 hours, and concentrated to a liquid. Distillation gives 2-bromobenzhydryl methyl ether as a pale yellow liquid, b.p. 125°–128°C./ 0.2 mm.

b. A solution of 11.1 g. of 2-bromobenzhydryl methyl ether in 23 ml. of tetrahydrofuran and 7 ml. of hexane is cooled to −50°C. and 22 ml. of butyllithium is introduced while maintaining the temperature below −50°C. The solution is stirred for 2 hours at −60° to −70°C. To the suspension is then added a solution of 5 g. of 4-oxo-tetrahydropyran in 5 ml. of tetrahydrofuran over a span of a few minutes. The mixture is stirred at −60°C. for 3 hours and at ambient temperature overnight. Ice-water is added, the organic layer is separated, the aqueous layer is extracted with methylene chloride and the combined organic solutions are dried over sodium sulfate. The solvent is removed under reduced pressure and subjected to column chromatography over alumina. Elution with benzene removes benzhydryl methyl ether, and the column is then eluted with diethyl ether. The solid obtained is heated at reflux in 60 ml. of glacial acetic acid, and then the solvent is removed under reduced pressure to leave a crystalline solid. This solid is recrystallized from hexane to give 1,2′,3,3′,5′,6′-hexahydro-3-phenylspiro[isobenzofuran-1,4′-pyran] as colorless crystals, m.p. 132°–134°C.

c. A solution of 1.3 g. of 1,2′,3,3′,5′,6′-hexahydro-3-phenylspiro(isobenzofuran-1,4′-pyran) in 20 ml. of tetrahydrofuran is cooled and treated dropwise with 4.5 ml. of butyllithium in hexane. The solution is stirred at −10°C. for 60 minutes, and 1.1 g. of dimethylaminoethyl chloride in 5 ml. of tetrahydrofuran are added slowly. The solution is placed under a nitrogen atmosphere and stirred for an additional hour at −10°C., then overnight at ambient temperature. Ice is added, the organic layer is separated, and the aqueous phase is extracted 4 times with ethyl ether. The organic solutions are combined, dried, and concentrated to a colorless oil, which is converted to a crystalline hydrochloride. The salt is recrystallized from an ethanol-water mixture to give crystals, m.p. 273°–274°C. dec., of 3-dimethylaminoethyl-1,2′,3,3′,5′,6′-hexahydro-3-phenylspiro[isobenzofuran-1,4′-pyran] hydrochloride.

Analysis: Calculated for $C_{22}H_{27}NO_2 \cdot HCl$: 70.66% C; 7.54% H; 3.74% N; 9.48% Cl. Found: 70.44% C; 7.54% H; 3,75% N; 9.58% Cl.

EXAMPLE 2

By following the manipulative procedure described above in Example 1c, 3-dimethylaminopropyl chloride is reacted with 1,2′,3,3′,5′,6′-hexahydro-3-phenyl-spiro(isobenzofuran-1,4′-pyran). The hydrochloride salt of the product is recrystallized from an acetone-ethyl ether mixture to give 3-(3-dimethylaminopropyl)-1,2′,3,3′,5′,6′-hexahydro-3-phenylspiro[isobenzofuran-1,4′-pyran] hydrochloride, m.p. 234.5°–235.5°C.

Analysis: Calculated for $C_{23}H_{29}NO_2 \cdot HCl$: 71.20% C; 7.79% H; 3.61% N; 9.14% Cl. Found: 70.96% C; 7.76% H; 3.58% N; 9.19% Cl.

By following the manipulative procedure described in Example 2, but substituting 3-diethylaminopropyl chloride and diisopropylaminopropyl chloride for 3-dimethylaminopropyl chloride, the following novel compounds are obtained:

3-(3-dietylaminopropyl)-1,2′,3,3′,5′,6′-hexahydro-3-phenylspiro [isobenzofuran-1,4′-pyran] hydrochloride; and 3-(3-diisopropylaminopropyl)-1,2′,3,3′,5′,6′-hexahydro-3-phenyl-spiro[isobenzofuran-1,4′-pyran] hydrochloride.

EXAMPLE 3 a. A solution of 27.7 g. of 2-bromobenzhydryl methyl ether in 38 ml. of tetrahydrofuran and 14 ml. of hexane is cooled to −50°C., 53 ml. of n-butyllithium are introduced dropwise while maintaining the temperature below −50°C., and the solution is stirred for 2 hours at −60° to −70°C. To the mixture is slowly added a solution of 10.7 g. of N-methyl-4-piperidone in 15 ml. of tetrahydrofuran, and the resulting suspension is stirred for an additional 3 hours at −60° to −70°C., and at ambient temperature overnight. Ice is added portionwise, the organic layer is separated and the aqueous layer is extracted with chloroform. The chloroform extract and the original organic layer are combined, dried, and concentrated under reduced pressure to an oil. The oil is diluted with benzene, and the solution is extracted with 15 ml. of 3N hydrochloric acid. Crystals begin to separate after a few minutes. The aqueous suspension is heated at 110°C. for 10 minutes and the solvent is removed under reduced pressure. The solid residue is dissolved in 60 ml. of glacial acetic acid containing 15 ml. of concentrated hydrochloric acid and the solution is refluxed for 10 minutes and allowed to stand at ambient temperature overnight. Ice water is added to the solution, and the solution is made basic with 40% sodium hydroxide. The precipitate which separates is collected and recrystallized from hexane to give colorless crystals, m.p. 123°–124°C., of 1,3-dihydro-1′-methyl-3-phenylspiro[isobenzofuran-1,4′-piperidine].

b. A stirred solution of 1.4 g. of 1,3-dihydro-1′-methyl-3-phenylspiro[isobenzofuran-1,4′-piperidine] in 20 ml. of tetrahydrofuran is cooled to −10°C. under nitrogen and treated dropwise with 4 ml. of n-butyllithium. Stirring is continued for 30 minutes, effecting a dark-red solution. To this solution is added 0.8 g. of dimethylaminoethyl chloride in 10 ml. of tetrahydrofuran and the reaction mixture is stirred overnight at ambient temperature, ice water is added, the organic layer is separated, the aqueous layer is extracted with ether, the ether extract and the original organic layer are combined, and dried. The solvent is removed, leaving a colorless oil which is converted to a crystalline hydrochloride. The salt is recrystallized from a 2-propanol-acetone-ethyl acetate mixture to give colorless crystals, m.p. 282°–284°C., of 1,3-dihydro-3-dimethylaminoethyl-1′-methyl-3-phenylspiro[isobenzofuran-1,4′-piperidine] dihydrochloride.

Analysis: Calculated for $C_{23}H_{30}N_2O \cdot 2HCl$: 65.23% C; 7.62% H; 6.61% N; 16.74% Cl. Found: 65.04% C; 7.62% H; 6.24% N; 16.53% Cl.

By following the manipulative procedure described in Example 3b, but substituting diethylaminoethyl chloride, diisopropylaminoethyl chloride and di-n-butylaminoethyl chloride for dimethylaminoethyl chloride, the following novel compounds are obtained:

1,3-dihydro-3-diethylaminoethyl-1'-methyl-3-phenyl-spiro[isobenzofuran-1,4'-piperidine] dihydrochloride;

1,3-dihydro-3-diisopropylaminoethyl-1'-methyl-3-phenylspiro-[isobenzofuran-1,4'-piperidine] dihydrochloride; and 1,3-dihydro-3-di-n-butylaminoethyl-1'-methyl-3-phenylspiro-[isobenzofuran-1,4'-piperidine] dihydrochloride.

EXAMPLE 4

By following the manipulative procedure described in Example 3b, reaction of 3-dimethylaminopropyl chloride with 1,3-dihydro-1'-methyl-3-phenyl-spiro[isobenzofuran-1,4'-piperidine] results in the preparation of 1,3-dihydro-3-(3-dimethylaminopropyl)-1'-methyl-3-phenylspiro[isobenzofuran-1,4'-piperidine] as the dihydrochloride. The salt is recrystallized from an ethanol-acetone-ether mixture to give the product as rhombic crystals, m.p. 266°–267°C., dec.

Analysis: Calculated for $C_{24}H_{32}N_2O \cdot 2HCl$: 65.88% C; 7.83% H; 6.40% N; 16.21% Cl. Found: 65.67% C; 8.00% H; 6.15% N; 16.02% Cl.

EXAMPLE 5 a. 17 ml. of thionyl chloride are added dropwise with cooling over a 30 minute span to a stirred suspension of 54.4 g. of finely powdered 2-bromo-N-(1-hydroxy-2-methyl-2-propyl)benzamide and 500 ml. of toluene. During addition a solution forms and then a solid begins to separate. The mixture is stirred at 0°C. for 30 minutes, at ambient temperature for 4 hours, and filtered. The solid is washed with 100 ml. of toluene and dried at 45°/50 mm. The solid is stirred in cold 10% sodium hydroxide, and the mixture is extracted with ether. The ether solution is dried over potassium carbonate and concentrated to an oil. Crystallization from hexane gives colorless crystals, m.p. 38°–40°C., of 2-(2-bromophenyl)-4,4-dimethyl-2-oxazoline.

b. A solution of 8.6 g. of 2-(2-bromophenyl)-4,4-dimethyl-2-oxazoline in 100 ml. of tetrahydrofuran is added dropwise over a 30 minute span to a stirred refluxing mixture of 1.0 g. of magnesium shavings and 25 ml. of tetrahydrofuran. After 2 hours at reflux, a solution of 2.5 g. of tetrahydrothiopyran-4-one in 10 ml. of tetrahydrofuran is added dropwise. This mixture is stirred under reflux for 1 hour and at ambient temperature for an additional hour, diluted with water and extracted with chloroform. The chloroform solution is dried over potassium carbonate and concentrated to a solid. The solid is triturated with ether to give colorless crystals which are recrystallized from ethanol to give colorless crystals, m.p. 181°–182°C., of 4-[2-(4,4-dimethyl-2-oxazoline-2-yl)phenyl)]-4-hydroxy-2,3,5,6-tetrahydrothiopyran.

c. A solution of 3.1 g of 4-[2-(4,4-dimethyl-2-oxazoline-2-yl)-phenyl)]-4-hydroxy-2,3,5,6-tetrahydrothiopyran in 70 ml. of 3N hydrochloric acid is stirred for 1 hour at 100°C., and the solution is cooled to 0°C. The crystals which separate are collected, washed with water, and recrystallized from benzene to give colorless crystals, m.p. 165°–166°C., of 1,3-dihydrospiro-[isobenzofuran-1,4'-tetrahydrothiopyran)]-3-one.

d. A solution of 3.4 g. of 1,3-dihydrospiro[isobenzofuran-1,4'-tetrahydrothiopyran]-3-one in 200 ml. of tetrahydrofuran is added dropwise to a stirred solution of 23 ml. of 2N phenyl-lithium in benzene-ether (7:3). After addition the solution is stirred for 3 hours at ambient temperature and poured into water. The mixture is extracted with ethyl acetate and the solvent is removed, leaving crystals. The crystals are triturated with benzene and then recrystallized from ethanol to give colorless crystals, m.p. 155°–157°C., of 1,2',3,3',-5',6'-hexahydro-3-hydroxy-3-phenylspiro[isobenzofuran-1,4'-thiopyran].

e. A solution of 26.0 g. of 1,2',3,3',5',6'-hexahydro-3-hydroxy-3-phenylspiro[isobenzofuran-1,4'-thiopyran] in 200 ml. of tetrahydrofuran is added dropwise to a stirred solution of 6.2 g. of lithium aluminum hydride in 200 ml. of tetrahydrofuran. The solution is stirred at ambient temperature for 30 minutes, refluxed for 1 hour, cooled to ambient temperature and carefully treated with 2 l. of water. The solution is extracted with chloroform, the organic phase is dried, and the solvent is removed, leaving an oil. Crystallization from benzene provides colorless crystals, m.p. 129°–132°C., of 4-hydroxy-4-(α-hydroxy-α-phenyl-2-tolyl)-2,3,5,6-tetrahydrothiopyran.

f. 12.0 g. of 4-hydroxy-4-(α-hydroxy-α-phenyl-2-tolyl)-2,3,5,6-tetrahydrothiopyran are dissolved in 115 ml. of glacial acetic acid and 13.5 ml. of concentrated hydrochloric acid. The solution is refluxed for 5 minutes, and cooled to ambient temperature. The precipitate which separates is collected and recrystallized from cyclohexane to give colorless crystals, m.p. 148°–149°C., of 1,2',3,3',5',6'-hexahydro-3-phenyl-spiro[isobenzofuran-1,4'-thiopyran].

g. A solution of 1.7 g. of 1,2',3,3',5',6'-hexahydro-3-phenylspiro[isobenzofuran-1,4'-thiopyran] in 25 ml. of tetrahydrofuran is cooled to −10°C. and a solution of 3.3 ml. of n-butyllithium in hexane (2.1 M) is added dropwise. The dark-red solution is stirred under nitrogen at −10° to −20°C. for 30 minutes, and then a solution of 0.7 g. of dimethylaminoethyl chloride in 10 ml. of tetrahydrofuran is added over a 5 minute span. The reaction mixture is stirred overnight at ambient temperature and water is added. The mixture is extracted with ether, the organic solution is dried, and ethereal hydrogen chloride is added to cause precipitation of the hydrochloride salt. Recrystallization from an acetone-diethyl ether mixture gives shiny prisms, m.p. 245°–246°C., of 3-dimethylaminoethyl-1,2',3,3',5',6'-hexahydro-3-phenylspiro[isobenzofuran-1,4'-thiopyran] hydrochloride.

Analysis: Calculated for $C_{22}H_{27}NOS \cdot HCl$: 67.72% C; 7.23% H; 3.59% N; 9.08% Cl; 8.22% S. Found: 67.44% C; 7.34% H; 3.36% N; 8.87% Cl; 7.98% S.

EXAMPLE 6

A solution of 1.41 g. of 1,2',3,3',5',6'-hexahydro-3-phenylspiro[isobenzofuran-1,4'-thiopyran] (Example 5f), in 25 ml. of tetrahydrofuran is cooled to −40°C. and a solution of 2.9 ml. of n-butyllithium in hexane (2.1 M) is added dropwise. The dark solution is stirred under nitrogen at −40° to −50°C. for 30 minutes and 0.67 g. of 3-dimethylaminopropyl chloride in 15 ml. of tetrahydrofuran are added over a 5 minute span. Stirring is continued overnight at ambient temperature and water is added. The mixture is extracted with chloroform and the organic solution is dried and concentrated to colorless crystals. Recrystallization from petrolium ether (b.p. 30°–60°C.) gives colorless prisms, m.p. 79°–79.5°C., of 3-(3-dimethylaminopropyl)-1,2',3,3',-

5',6'-hexahydro-3-phenylspiro[isobenzofuran-1,4'-thiopyran].

Analysis: Calculated for $C_{23}H_{29}NOS$: 75.15% C; 7.95% H; 3.81% N; 8.72% S. Found: 75.08% C; 8.12% H; 3.55% N; 8.63% S.

By following the manipulative procedure described in Example 6, but substituting 3-diethylaminopropyl chloride and 3-diisopropylaminopropyl chloride for 3-dimethylaminopropyl chloride, the following novel compounds are obtained:

3-(3-diethylaminopropyl-1,2',3,3',5',6'-hexahydro-3-phenylspiro[isobenzofuran-1,4'-thiopyran]; and 3-(3-diisopropylaminopropyl)-1,2',3,3',5',6'-hexahydro-3-phenylspiro [isobenzofuran-1,4'-thiopyran].

We claim:

1. A compound of the formula

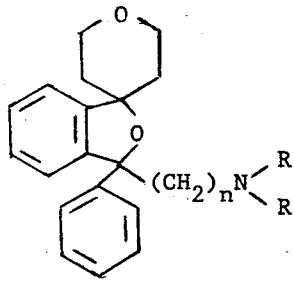

wherein R is a linear alkyl of from 1 to 4 carbon atoms or isopropyl and $n$ is the integer 2 or 3; and the physiologically acceptable acid addition salts thereof.

2. A compound as defined in claim 1, wherein R is methyl or ethyl; and the physiologically acceptable acid addition salts thereof.

3. The compound as defined in claim 2 which is 3-dimethylaminoethyl-1,2',3,3',5',6'-hexahydro-3-phenylspiro-[isobenzofuran-1,4'-pyran]; and the physiologically acceptable acid addition salts thereof.

4. The compound as defined in claim 2 which is 3-(3-dimethylaminopropyl)-1,2',3,3',5',6'-hexahydro-3-phenylspiro[isobenzofuran-1,4'-pyran]; and the physiologically acceptable acid addition salts thereof.

5. A method of depressing the central nervous system which comprises administering to a patient an effective amount of a compound defined in claim 1.

6. An orally administrable composition which consists essentially of a pharmaceutically acceptable carrier and from about 0.5 to 100 mg. of a compound as defined in claim 1.

* * * * *

UNITED STATES PATENT AND TRADEMARK OFFICE
CERTIFICATE OF CORRECTION

PATENT NO. : 3,957,828
DATED : May 18, 1976
INVENTOR(S) : Victor J. Bauer, et al It is certified that error appears in the above—identified patent and that said Letters Patent are hereby corrected as shown below:

Column 1, lines 50 - 55, change 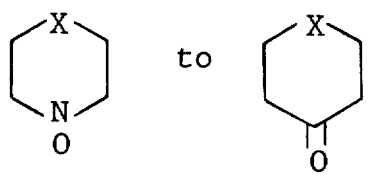

Column 6, line 9, change "3-(3-dietyl..." to --3-(3-diethyl...--;

Column 7, line 11, change "spiro-[iso" to --spiro[iso--;

Column 7, lines 58 and 61, change "oxazoline-2" to --oxazolin-2 --;

Column 8, line 2, change "phenyl-lithium" to --phenyllithium--;

Column 8, line 67, change "petrolium" to --petroleum--.

Signed and Sealed this

Seventh Day of September 1976

[SEAL]

Attest:

RUTH C. MASON
*Attesting Officer*

C. MARSHALL DANN
*Commissioner of Patents and Trademarks*